US009068909B2

(12) United States Patent
Knox et al.

(10) Patent No.: US 9,068,909 B2
(45) Date of Patent: Jun. 30, 2015

(54) NONDESTRUCTIVE TEST FOR FLEXIBLE COMPOSITES

(75) Inventors: John Graeme Knox, Oxford, MI (US); Tulin K. Markes, West Bloomfield, MI (US)

(73) Assignee: GATES CORPORATION, Denver, CO (US)

( * ) Notice: Subject to any disclaimer, the term of this patent is extended or adjusted under 35 U.S.C. 154(b) by 674 days.

(21) Appl. No.: 13/312,526

(22) Filed: Dec. 6, 2011

(65) Prior Publication Data
US 2012/0151989 A1 Jun. 21, 2012

Related U.S. Application Data

(60) Provisional application No. 61/424,449, filed on Dec. 17, 2010.

(51) Int. Cl.
*G01M 7/00* (2006.01)
*G01N 3/30* (2006.01)
*G01N 3/32* (2006.01)
*G01P 15/00* (2006.01)
*G01M 7/08* (2006.01)
*G01N 3/20* (2006.01)

(52) U.S. Cl.
CPC .......... *G01N 3/30* (2013.01); *G01N 2203/0069* (2013.01); *G01M 7/08* (2013.01); *G01N 3/20* (2013.01); *G01N 2203/0039* (2013.01); *G01N 2203/0076* (2013.01); *G01N 2291/0231* (2013.01)

(58) Field of Classification Search
CPC ............. G01M 7/08; G01N 3/20; G01N 3/30; G01N 2291/0231; G01N 2291/02827
USPC ............................. 73/12.01, 12.09, 12.13, 82
See application file for complete search history.

(56) References Cited

U.S. PATENT DOCUMENTS 3,333,461 A * 8/1967 Gordon et al. ............... 73/769
4,305,433 A * 12/1981 Vanassche et al. ........ 139/425 A
4,519,245 A 5/1985 Evans
(Continued)

FOREIGN PATENT DOCUMENTS

CN 2476808 Y 2/2002
CN 101561379 A 10/2009
(Continued)

OTHER PUBLICATIONS

Author: Ajay Kapadia, Title: Non Destructive Testing of Composite Materials, Date: Aug. 7, 2007, Publisher: National Composites Network, pp. i-iv and 1-18.*
Authors: J. J. Peters, D. J. Barnard, N. A. Hudelson, T. S. Simpson, and D. K. Hsu, Title: A prototype tap test imaging system: Initial field test results, Date: Yr.2000, Publisher: AIP Publishing, AIP Conference Proceedings 509, 2053, pp. bibsheet and 2053-2060.*
(Continued)

*Primary Examiner* — Harshad R Patel
(74) *Attorney, Agent, or Firm* — Paul N. Dunlap, Esq.; Jeffrey A. Thurnau, Esq.

(57) ABSTRACT

A method for testing internal differences in reinforced flexible composites including placing a flexible composite on a rigid support structure, tapping the composite with a tapper of predetermined mass, determining a value representative of the impact duration of the tap and/or computing a value representative of the local stiffness of the composite. The composite may be a power transmission belt or portion thereof with tensile cord reinforcement. The method is useful for comparing the degree of penetration of elastomer into the tensile cord, for example in a cast polyurethane toothed belt.

15 Claims, 2 Drawing Sheets

(56) References Cited

U.S. PATENT DOCUMENTS

| | | | |
|---|---|---|---|
| 4,542,639 | A | 9/1985 | Cawley et al. |
| 5,048,320 | A | 9/1991 | Mitsuhashi et al. |
| 5,239,184 | A | 8/1993 | Mancosu et al. |
| 5,807,194 | A | 9/1998 | Knutson et al. |
| 5,891,561 | A | 4/1999 | Kinoshita et al. |
| 6,327,921 | B1 | 12/2001 | Hsu et al. |
| 6,450,035 | B1 | 9/2002 | Nishizono |
| 6,748,791 | B1 * | 6/2004 | Georgeson et al. .......... 73/12.13 |
| 7,583,413 | B2 | 9/2009 | Nojiri et al. |
| 7,647,809 | B1 * | 1/2010 | Cooney ........................ 73/12.01 |
| 2006/0145031 | A1 | 7/2006 | Ishikawa et al. |
| 2011/0218069 | A1 * | 9/2011 | Nakashima et al. .......... 474/260 |

FOREIGN PATENT DOCUMENTS

| | | | |
|---|---|---|---|
| JP | 5338752 | A | 12/1993 |
| JP | 2002343989 | A | 11/2002 |
| SU | 1685691 | A1 | 10/1991 |

OTHER PUBLICATIONS

David K. Hsu, Daniel J. Barnard, John J. Peters, and Vinay Dayal, "Physical basis of tap test as a quantitative imaging tool for composite structures on aircraft," AIP Conf. Proc.—May 23, 2000—vol. 509, pp. 1857-1864, Review of Progress in Quantitative Nondestructive Evaluation: vol. 19 (ISBN: 1-56396-930-0).

Dear J P: "High Speed Photography of Impact Effects in Three-Point Bend Testing of Polymers", Journal of Applied Physics, American Institute of Physics, New York, US, vol. 67, No. 9, Part 01, May 1, 1990, pp. 4304-4312, XP000107827, ISSN: 0021-8979, DOI: 10.1063/1.344946.

European Patent Office, International Search Report, Mailing date Feb. 20, 2012.

Japanese Patent Office, Office Action for Japanese patent application No. 2013-544558, Mailing date: Sep. 2, 2014.

* cited by examiner

NONDESTRUCTIVE TEST FOR FLEXIBLE COMPOSITES

CROSS REFERENCE TO RELATED APPLICATIONS

This application claims the benefit of U.S. Provisional Patent Application Ser. No. 61/424,449 filed on Dec. 17, 2010.

BACKGROUND OF THE INVENTION

1. Field of the Invention

This invention relates generally to a nondestructive test method for flexible composite articles, more particularly to a method of testing cord penetration in reinforced rubber articles, and specifically to a test for cord penetration in polyurethane power transmission belts.

2. Description of the Prior Art

A number of nondestructive test methods are known for structures of rigid composites and metals. Examples of such methods include use of ultrasonics, eddy currents, and acoustics. Composite or metal structures can often be tested for internal defects by tapping on them and listening for differences in the sound of the tap. The so-called coin tap test or simply, "tap testing" has been applied to various types of structures of rigid materials, including honeycomb composites, aircraft, space structures, buildings, etc. Tap testing may be used to detect delamination, crushed or missing internal support structures, debonding, etc. in such rigid structures. Tap testing systems range from hand-tapping by a person with a trained ear, to automated tappers with electronic analysis of the sound or impulse.

U.S. Pat. No. 6,327,921 to Hsu et al. describes a nondestructive, tap-testing, inspection system which provides an image-based display of a plurality of structural stiffness measures, each stiffness measure calculated from a measure of impact duration for a "tap" useful for aircraft structures and composite and metal honeycomb structures. Other examples of tap-testing systems are disclosed in U.S. Pat. No. 5,048,320 to Mitsuhashi et al. and in U.S. Pat. No. 4,519,245 to Evans.

Flexible composite articles, such as tires, power transmission belts and hose, may have internal defects such as voids, delaminations, and the like. U.S. Pat. No. 5,891,561 to Kinoshita et al. describes the use of load carrying cords of aramid or other fibers in rubber power transmission belts. According to that patent, when treating the cords with resorcinol-formaldehyde-latex ("RFL") treatments, if the percentage of voids after treatment is greater than 1.5%, the voids become relatively large, and the cohesion between filaments in the cords decreases and a fraying problem becomes significant. The method proposed to determine the percentage of voids is to enlarge a cross section of the cord with an electron microscope to allow precise area measurements.

U.S. Pat. No. 5,807,194 to Knutson et al. describes the history of cord development for belts with cast polyurethane bodies, emphasizing the importance of cord penetration by the various treatments or belt materials used. For the carbon cords of primary interest, Knutson et al. propose a destructive test for measuring cord penetration. According to that patent, the amount of belt material that a cord picks up during casting can be measured by weighing a length of greige cord and comparing it to a cord that is dislodged from a finished belt and measuring the weight difference. In this manner, cord pick up of belt material in mg per $mm^3$ of cord volume can be determined for each millimeter of cord length. In practice this test may be confirmed by studying magnified cross sections of the cord.

Both cord weighing and cross-section analyses are destructive tests.

SUMMARY

The present invention is directed to systems and methods which provide a nondestructive test method for flexible composite articles, useful for testing cord penetration in reinforced rubber articles such as tires, hose, and belts. The present invention is useful for testing cord penetration in carbon-fiber reinforced, polyurethane, power transmission belts.

The invention is directed to a method for testing internal variations or differences within or between reinforced flexible composites including the steps of supporting a flexible composite article, e.g. by placing it on a rigid support structure, tapping the composite with a tapper of predetermined mass, determining a value representative of the impact duration of the tap and/or computing a value representative of the local stiffness of the composite. The composite may be a power transmission belt or portion thereof with tensile cord reinforcement. The composite may be a slab of belts or portion thereof. The support structure may be a mandrel, pulley or a flat plate and may have protrusions to fit the belt profile. The method is useful for comparing the degree of penetration of elastomer into the tensile cord, for example in a cast polyurethane toothed belt.

In various embodiments, the tapper may be an instrumented accelerometer hammer or pendulum, which may be manually operated or automated. The impact duration may be evaluated by a computer. The measurements may be taken over an area and a graphical representation generated. The article may be held in a stressed state or supported in a substantially unstressed state.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The accompanying drawings, which are incorporated in and form part of the specification in which like numerals designate like parts, illustrate embodiments of the present invention and together with the description, serve to explain the principles of the invention. In the drawings.

DETAILED DESCRIPTION

Figure 1:
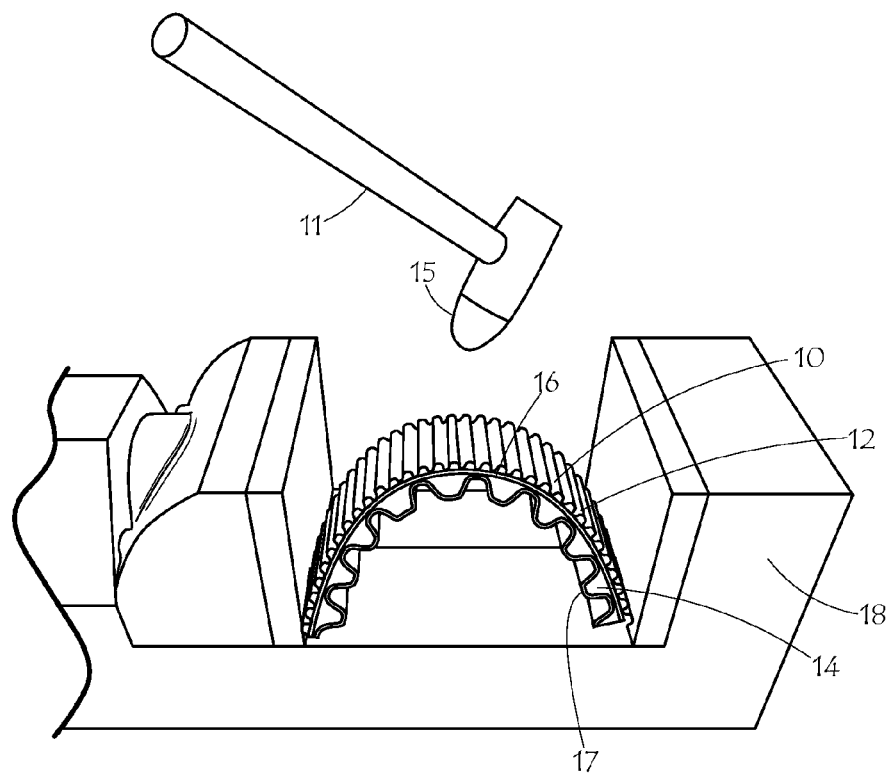
FIG. 1 illustrates a test sample and test arranged according to an embodiment of the invention.

Flexible composites include various laminated or fiber-reinforced elastomeric articles, such as tires, belts, hose, air springs, diaphragms, and the like. Various internal manufacturing variations and/or defects are possible in such articles, including voids, delamination, foreign matter, or the like. Internal defects may also arise during service, such as delamination, crimps or fatigued regions, fiber breakage, or the like. The conventional approach to identifying internal defects or variations in flexible composites is by destructive testing, i.e., by dissecting the composite and examining it visually, often under magnification. The inventors have discovered that tap testing is capable of revealing subtle differences in composite structure heretofore only known to be discoverable by destructive testing methods. A tap test involves tapping the sample in question with an accelerometer equipped with a tip. Any suitable tip material and tip shape for the sample being tested may be used. The accelerometer's output signal from a tap is a voltage pulse that represents the force-time history of the impact process. The voltage pulse may be followed by a small undershoot where the output voltage goes slightly negative and then recovers toward zero. Differences in the voltage pulses from different regions of the article being tested may be indicative of internal structural variation. Pulse differences may involve both the amplitude and the width of the voltage pulse. Likewise differences in the impact pulses from different articles may be indicative of internal structural variation between articles.

According to an embodiment of the invention, a flexible composite may be tapped, preferably with a calibrated mass or force, and the sound may be analyzed, preferably with electronic circuitry. In a preferred test method, the flexible composite is tapped with a piezoelectric accelerometer as the tapping mass, and the electronic circuitry measures the contact time between the mass and the sample. The contact time, $\tau$ (which is typically a few hundred microseconds) can be converted to the local spring stiffness k (expressed in mega-Newtons per meter) and used as a measure of the mechanical condition of flexible composite. A simple spring model yields the relationship, $\tau = \pi \sqrt{m_T/k}$, where $m_T$ is the mass of the tapper. An advantage of using the contact time measurement is that it is relatively insensitive to various measurement variables such as the tapper's material properties, radius and velocity. Such variables may all have greater affects on the pulse amplitude. Instead of actual contact time, a value representative of the contact time may be used. Likewise, instead of the stiffness, a value representative of the stiffness may be used, resulting in comparative measurements. It may often be sufficient for a given test application to merely compare an unknown specimen to a control or known sample. The comparison may involve impulse duration or contact time or a derived value such as stiffness or a value representative of the stiffness.

U.S. Pat. No. 6,327,921 to Hsu et al., the contents of which are hereby incorporated herein by reference, describes an exemplary nondestructive, tap-testing, inspection system which provides an image-based display of a plurality of structural stiffness measures, each stiffness measure calculated from a measure of impact duration for a "tap." In the conventional use of a tap test on rigid structures, the sound of the tap is considered "duller" in regions with internal structural damage than in good regions. This dull sound corresponds to a wider pulse width for the impact or tap. Flexible composites would not be expected to be good candidates for tap testing because materials such as rubber or other elastomers are naturally much more damping than rigid structural materials and therefore sound "dull" with or without any internal damage or structural variation. The internal damage is also likely to be much more subtle in a flexible composite than the typical damage tested by tapping on rigid structures. Tapping on rigid structures may for example locate studs in walls, or crushed honeycomb structures, or missing features. For flexible articles, one may be interested in finding small voids or inclusions, or minor differences in material properties of a reinforcing component.

Unlike the conventional application of tap testing to self supporting structures or rigid articles, the testing of flexible composites is best carried out with the flexible composite article held still in some kind of holder or mounted on a support structure for testing. It may also be preferable to hold the flexible composite in a way that applies stress to the region to be tapped. One suitable method to apply stress to a flexible composite is by bending. Another is by tensioning it. Suitable holders for a flexible composite article may be readily adapted or designed by those of skill in the art. As an example, a simple vise may be used to hold many types of flexible articles in a stressed state. In a preferred embodiment, a toothed belt is held in an unstressed state with rigid support under the region to be tapped. Thus, the test region is sandwiched between the tapper and the rigid support when struck. This is believed to minimize unwanted vibrations of the composite as a whole and emphasize the internal vibration response of the materials.

FIG. 1 illustrates a tap test according to the present invention applied to a section of a power transmission belt. In FIG. 1, belt 10 is held in vise 18 for tapping with instrumented accelerometer hammer 11 having tip 15. Belt 10 includes elastomeric belt body 12 with teeth 14 for synchronous motion control or power transmission. Belt 10 is reinforced with embedded tensile cord 16 and tooth cover 17. The belt sample is in a stressed state due to the bending or arching in the vise.

Figure 2:
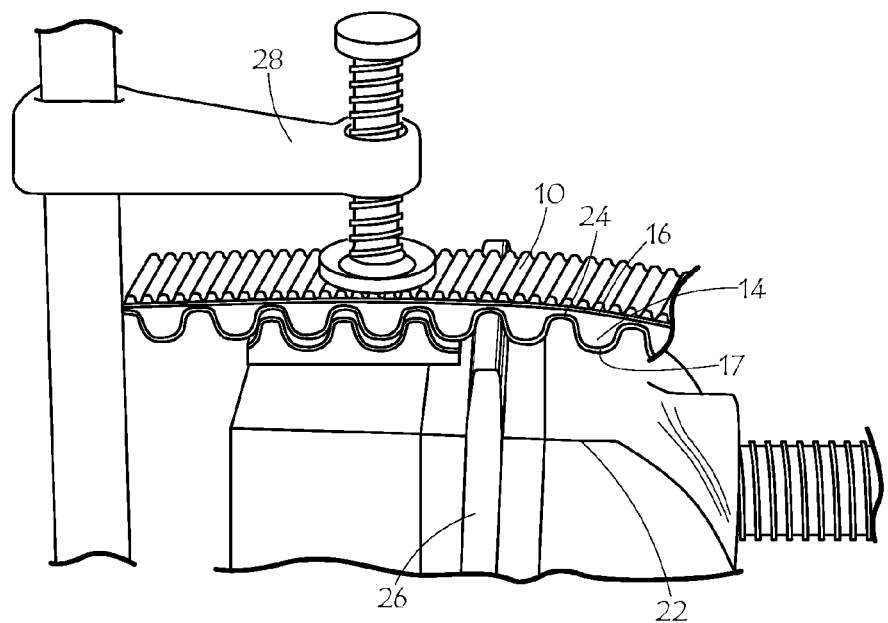
FIG. 2 illustrates a test sample and test arranged according to another embodiment of the invention.

FIG. 2 illustrates a tap test according to the present invention applied to a section of a power transmission belt. In FIG. 2, belt 10 is held in vise 28 for tapping with instrumented accelerometer hammer 11. Belt 10 includes elastomeric belt body 12 with teeth 14 for synchronous motion control or power transmission. Teeth 14 alternate with land regions 24. Vise 28 includes support plate 22 with one or more protrusions 26 which support one or more land regions 24. The belt may be tested by tapping on the back side over a supported land region. Belt 10 is again reinforced with embedded tensile cord 16 and tooth cover 17. In this test, the belt sample is in its natural unstressed state. Note that unstressed implies some curvature in this portion of belt 10 resulting from having been molded on a cylindrical mandrel.

Figure 3:
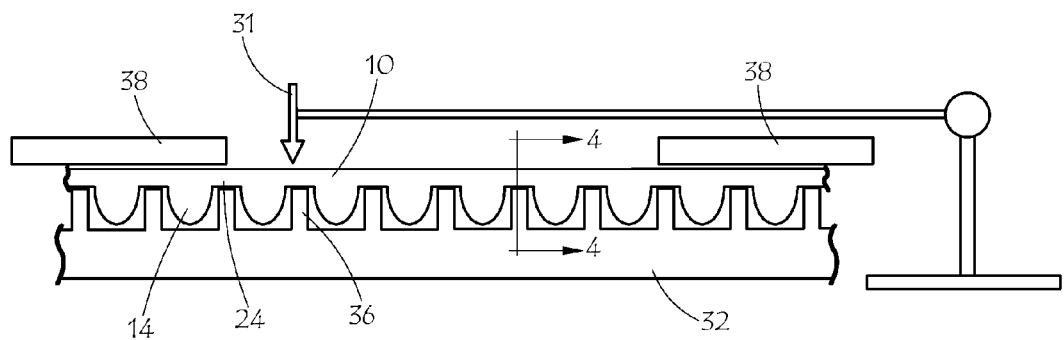
FIG. 3 illustrates a test sample and test arranged according to another embodiment of the invention.

FIG. 3 illustrates another tap test according to the present invention applied to a section of a power transmission belt. In FIG. 3, belt 10 is held in a pair of clamps 38 on support plate 32 for tapping with instrumented accelerometer pendulum 31. Teeth 14 alternate with land regions 24. Support plate 32 includes a number of protrusions 36 which support a number of land regions 24. The belt may be tested by tapping on the back side over a supported land region. Pendulum 31 may be automatically controlled to ensure minimal variation in tapping force, and to produce a desired number of repeated taps. In this test arrangement, the belt is held in a substantially unstressed state. A small amount of stress is imposed on the belt by flattening out the molded-in curvature previously mentioned.

Figure 4:
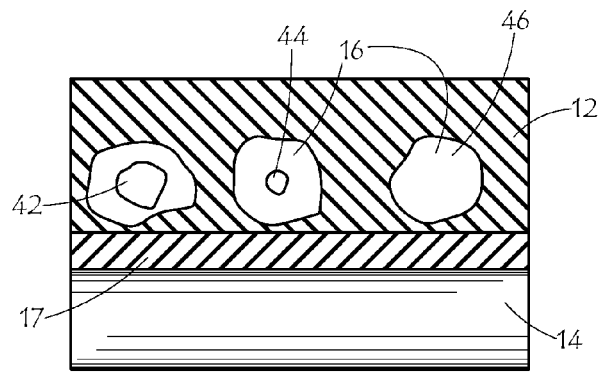
FIG. 4 is a cross-sectional representation of a belt to be tested according to an embodiment of the invention.

In order to illustrate the practical application of the inventive method, tap testing was applied to study cord penetration levels in carbon fiber reinforced, cast polyurethane, synchronous belts. Such belts have been described, for example, in U.S. Pat. No. 5,807,194 to Knutson et al. The Knutson patent describes a synchronous power transmission belt with a belt body of cast urethane belt material, belt teeth formed of the body and spaced apart at a pitch, a wear-resistant fabric reinforcement disposed along peripheral surfaces of the belt teeth, a tensile member of helically spiraled cord embedded in the belt body. The particular belt tested here had a 14-mm pitch and 54 k carbon fiber tensile cords. Two belts were produced, one with essentially complete (indicated as 99%) penetration of the urethane into the cord, and one exhibiting about 60% penetration of the urethane into the cord. These penetration values were determined by sectioning the belt, embedding the section in a resin, polishing the embedded section and determining the percent penetrated area by optical inspection. Of course, for the purposes of this conventional destructive testing, the belts had to be cut into a number of sections. FIG. 4 illustrates a partial cross section of such a belt including three cuts of the cord 16 embedded in elastomeric body 12, sectioned in a land area 24 between two teeth 14, where the cord is close to tooth cover 17. In FIG. 4, the three cord sections shown are representative of three different degrees of penetration of cast urethane into a carbon fiber bundle. Cord 46 is substantially fully penetrated by the polyurethane. Cord 44 has a small region near the center of the cord without penetration, and cord 42 has a large region without penetration. It should be understood that three such cords need not typically reside side-by-side in the same belt. More typically, a large section of belt, or even an entire belt, may consistently exhibit one characteristic degree of penetration. Alternately, a gradient in penetration may exist across a series of belts coming from the same build or slab, or there may be smaller regions of varying penetration. Thus, a method of rapidly testing large areas for differences in penetration would be advantageous. Likewise, FIG. 4 could be representative of voids or delaminations in fibrous reinforcements of elastomeric composite articles, cord 42 representing a larger void and cord 44 a smaller void. The inventive method is believed to be applicable to identify or quantify various such internal differences in compared samples of such elastomeric composites.

For the tap testing was chosen the so-called CATT (Computer Aided Tap Tester) which is an instrument developed by Iowa State University for aerospace nondestructive inspection, and licensed to Advanced Structural Imaging, Inc. (ASI) for commercialization. It employs a piezoelectric accelerometer as the tapping mass and measures the contact time between the mass and the sample with an electronic circuit. The contact time, τ (typically a few hundred microseconds) can be converted to the local spring stiffness, k (expressed in mega Newton per meter). This test has been used as a measure of the mechanical condition of an aerospace structure. The test can be repeated over a predetermined area and the results graphically mapped on a display device. The instrumented tapping mass was initially simply dropped from a certain height onto the sample. In further testing, a pendulum was used to better control the location of impact and the force of impact. The pendulum may be hand operated or automated. An automated pendulum permits control of the frequency of impact, which improves control and may prevent errors from multiple impacts or bouncing of the tapping mass.

In a first series of tests, a total of 6 samples were tested using the CATT. The samples were sections of the above-mentioned drive belts which each measured 140-mm long and 20-mm wide. The belt sections had ten large teeth on the inner surface and many small cogs on the outer surface. The belt body was of cast polyurethane and the tensile cord was of carbon fiber. Three of the samples were determined by destructive testing to have 99% penetration of the cord bundle by the cast polyurethane, and three samples were found to have only 60% penetration. To hold the samples, the samples were pre-loaded in bending into the shape of an arch, as shown in FIG. 1, and the taps were made on or near the top of the arch with the accelerometer. Each sample was tapped 20 to 30 times and the contact time data were averaged. Each contact time was converted into stiffness and the values were also averaged. The test results of the 6 samples are summarized in Table 1.

The three belts with 60% penetration showed remarkable consistency—their average τ values were 786, 798, and 799 µs respectively. In terms of stiffness, they were 0.233, 0.230, and 0.238 MN/m respectively. The results of the three belts with 99% penetration showed two of the belts were very close to each other (596 µs and 598 µs and 0.399 MN/m), and the third was slightly less stiff (649 µs and 0.342 MN/m). Even so, the separation between 99% and the 60% penetration belts was still clear cut and there was no overlap between the scattering of the data of the two groups of belts. Thus, it was shown that tap testing is capable of distinguishing between belts with high and moderate degrees of cord penetration.

TABLE 1

| Belt Sample | Ave. τ (µs) | Ave. k (MN/m) |
| --- | --- | --- |
| 99% penetration belt 1 | 598 | 0.399 |
| 99% penetration belt 2 | 596 | 0.406 |
| 99% penetration belt 3 | 649 | 0.342 |
| 60% penetration belt 1 | 799 | 0.238 |
| 60% penetration belt 2 | 786 | 0.233 |
| 60% penetration belt 3 | 798 | 0.230 |

In a second series of tests, three samples each of four different cord penetration levels (60%, 86%, 93-95%, 99%) were tested as in the first series using the CATT. Again, the samples were pre-loaded in bending into the shape of an arch, as shown in FIG. 1, and the taps were made on the top of the arch with the accelerometer. Each sample was tapped 20 to 30 times and the contact time data were averaged. Each contact time was converted into stiffness and the values were also averaged. The test results of the 12 samples are summarized in Table 2. It was found that the test did not resolve the difference between the 86% and 93-95% penetration samples. Neither changing the arch span nor changing the tapper force improved the resolution.

The second series of tests were then repeated on the 86% and 93-95% penetration samples using a different holder as illustrated in FIG. 2, one which supported a land region without bending or stressing the belt. The samples were tapped on the backside of the belt over the supported land region. Each sample was tapped 20 to 30 times and the contact time data were averaged. Each contact time was converted into stiffness and the values were again averaged. The test results of the 6 samples in the second holder are also summarized in Table 2. The contact time measured for 93-95% sample, belt 3 in particular, was not as consistent as the other belts. This is consistent with the optical analysis of that belt, which showed variation from cord to cord (whereas most samples were more consistent from cord to cord within the belt).

TABLE 2

| Belt Sample | Arched Sample Ave. τ (µs) | Supported Sample Ave. τ (µs) | Supported + Pendulum Ave. τ (µs) |
|---|---|---|---|
| 99% penetration belt 1 | 1478.6 | | |
| 99% penetration belt 2 | 1511.2 | | |
| 99% penetration belt 3 | 1462.2 | | |
| 93-95% penetration belt 1 | 1435.9 | 842.3 | 586.6 |
| 93-95% penetration belt 2 | 1577.4 | 826.1 | 560.6 |
| 93-95% penetration belt 3 | 1536.4 | 854.8 | 649.0 |
| 86% penetration belt 1 | 1478.5 | 884.6 | 622.7 |
| 86% penetration belt 2 | 1462.9 | 902.0 | 610.9 |
| 86% penetration belt 3 | 1498.3 | 853.1 | 620.5 |
| 60% penetration belt 1 | 2129.8 | | |
| 60% penetration belt 2 | 1996.2 | | |
| 60% penetration belt 3 | 1879.1 | | |

To improve the consistency of measurements, a pendulum tapper was used instead of a dropped mass. The striking location of a pendulum can be controlled more reproducibly, the height can be accurately controlled, and the frequency of striking can be controlled as well. The tests were then repeated on the 86% and 93-95% penetration samples using an automated pendulum tapper and the sample holder illustrated in FIG. 3. The results are shown in Table 2. This test produced the best differentiation between the 86% and 93-95% penetration samples. Note that the absolute values of the contact time depend on the type of holder arrangement utilized. The arrangement of FIG. 3 had the smallest variation or standard deviation for the 20 to 30 repeated taps. Note that belt 3 with 93-95% penetration again stands out as different from the others. This is believed due to the cord to cord variation within the belt as noted above.

It should be understood that with a suitable holder, a whole endless belt can likewise be tested without destroying the belt. The test can be extended to multiple locations for characterizing the entire width and length of the sample. Thus, the full capability of the CATT can be used to map out the response of the article under test and locate regions of different response. A particularly useful result of the fact a supported belt gives the best differentiation of small differences is that a toothed belt can be tested on a drive using a pulley or sprocket as the support. Thus, a belt can be tested for internal changes, damage or defects in situ at any stage of its life without removal from the drive. As another example, belts which are first built as large cylindrical slabs or sleeves may be rapidly mapped for internal differences, before or after removal of the slab from the mold tooling. The tooling on which the belt slabs are built can provide the needed support for the test. The testing can be carried out before various expensive finishing operations, such as cutting, grinding, labeling, or it can be carried out at any point in the process as desired. The test can easily be located anywhere in the process as it does not require special sample preparation, conditioning, or the like. For example, in belt cutting, the slab may be mounted on a mandrel which again may provide the support for utilizing a tap test on the slab.

Likewise, it is envisioned that other flexible composite articles, such as tires and hose, can be tested and/or compared for locating or identifying internal differences, using appropriate supporting holders and an instrumented tapper.

Although the present invention and its advantages have been described in detail, it should be understood that various changes, substitutions, and alterations can be made herein without departing from the scope of the invention as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. The invention disclosed herein may suitably be practiced in the absence of any element that is not specifically disclosed herein.

What is claimed is:

1. A method of testing internal structural variations within a flexible, elastomeric-matrix, composite article comprising an elastomeric matrix and a reinforcing fiber structure embedded therein, said method comprising the steps of:
   mounting said composite article in a fixed position;
   tapping the article;
   determining the impact duration of the tap; and
   comparing the impact duration to a reference value.

2. The method of claim 1 further comprising computing a value representative of the local stiffness of the article from the impact duration to be used in said comparison.

3. The method of claim 1 wherein said comparison indicates degree of penetration of said elastomeric matrix material into said reinforcing fiber structure.

4. The method of claim 1 wherein said composite article is a power transmission belt reinforced with tensile cord embedded in said belt.

5. The method of claim 1 wherein said mounting includes pre-stressing the article.

6. The method of claim 5 wherein said pre-stressing is a bending stress.

7. The method of claim 1 wherein said mounting includes placing a portion of the article to be tested on a rigid support structure for support in a substantially unstressed state.

8. A method of testing internal structural variations comprising:
   placing a flexible, elastomeric-matrix, composite article on a rigid support structure,
   tapping the composite with a tapper of predetermined mass,
   determining a value representative of the impact duration or contact time of the tap, and
   comparing the impact duration or contact time to a reference value;
   wherein the composite article comprises an elastomeric matrix and a reinforcing fiber structure embedded therein.

9. The method of claim 8 further comprising computing a value representative of the local stiffness of the composite.

10. The method of claim 8 wherein the tapper comprises an accelerometer.

11. The method of claim 8 further comprising repeating the tapping at various points over a predetermined area and producing a graphical representation of the stiffness over that area.

12. The method of claim 8 wherein the flexible, elastomeric-matrix, composite article is a power transmission belt or a portion thereof.

13. The method of claim 12 wherein the support structure is a pulley.

14. The method of claim 8 wherein the flexible, elastomeric-matrix, composite article is a belt slab or a portion thereof.

15. The method of claim 8 wherein the flexible, elastomeric-matrix, composite article is a toothed power transmission belt, and the support structure provides support in a land region between two belt teeth, and the tap is directed over the supported land region.

* * * * *